United States Patent [19]

Unvala

[11] Patent Number: 5,202,641

[45] Date of Patent: Apr. 13, 1993

[54] METHOD, TEST PROBE AND APPARATUS FOR THE MEASUREMENT OF ALTERNATING CURRENT POTENTIAL DROP BY CONFINING TEST CURRENT TO A SKIN REGION OF A TEST SPECIMEN

[75] Inventor: Bhikhu A. Unvala, London, England

[73] Assignee: Matalect Limited, London, England

[21] Appl. No.: 640,301

[22] PCT Filed: Jul. 26, 1989

[86] PCT No.: PCT/GB89/00849

§ 371 Date: Jan. 25, 1991

§ 102(e) Date: Jan. 25, 1991

[87] PCT Pub. No.: WO90/01159

PCT Pub. Date: Feb. 8, 1990

[30] Foreign Application Priority Data

Jul. 26, 1988 [GB] United Kingdom ............... 8817725

[51] Int. Cl.$^5$ ..................... G01R 27/14; G01N 27/20
[52] U.S. Cl. ................... 324/715; 324/718; 324/713; 324/603
[58] Field of Search ............ 324/713, 715, 716, 718, 324/720, 724, 602, 603, 263

[56] References Cited

U.S. PATENT DOCUMENTS 2,094,234  9/1937  Drain ................................ 324/718
3,699,436 10/1972  Shigematsu et al. ............... 324/715
4,266,185  5/1981  Charlesworth et al. ............ 324/718
4,683,419  7/1987  Neuelmann et al. ............... 324/718

Primary Examiner—Gerard R. Strecker
Assistant Examiner—Diep Do
Attorney, Agent, or Firm—Richard M. Goldberg

[57] ABSTRACT

A method of alternating current potential drop measurement is provided in which the flow of the current in the specimen is laterally confined by passing the applied current externally over and in the immediate proximity to the surface of the specimen. To this end, a voltage probe is provided having a longitudinally extending isolated conductor which is connected to one current contact of a pair of current contacts. In use, this is arranged to provide an external flow path for current applied to the specimen. The isolated conductor is arranged to lie adjacent to the voltage probe contacts. For convenience of mounting, the conductor may be implemented as a conductive track on a printed circuit board. The track may also be bifurcated in order to accommodate one or more short lengths of conductor which can be used to form one or more compensating inductive loops which latter may be wired to afford cancellation of picked-up induced emf. Preferably, the sensed voltage is referred to a phase sensitive detector to which a reference waveform voltage in phase with the current is applied.

14 Claims, 6 Drawing Sheets

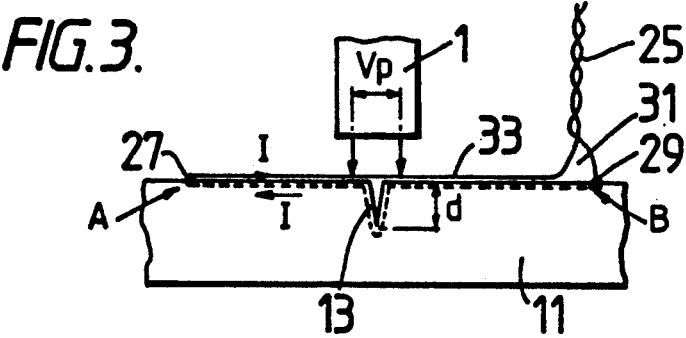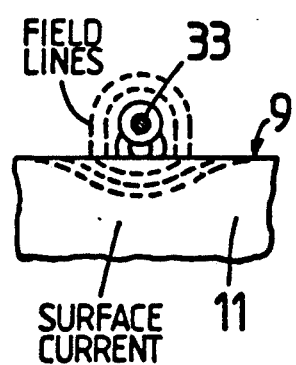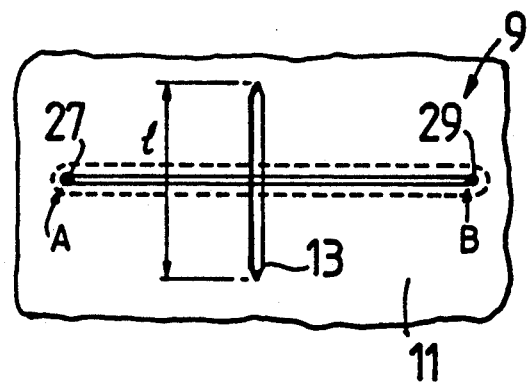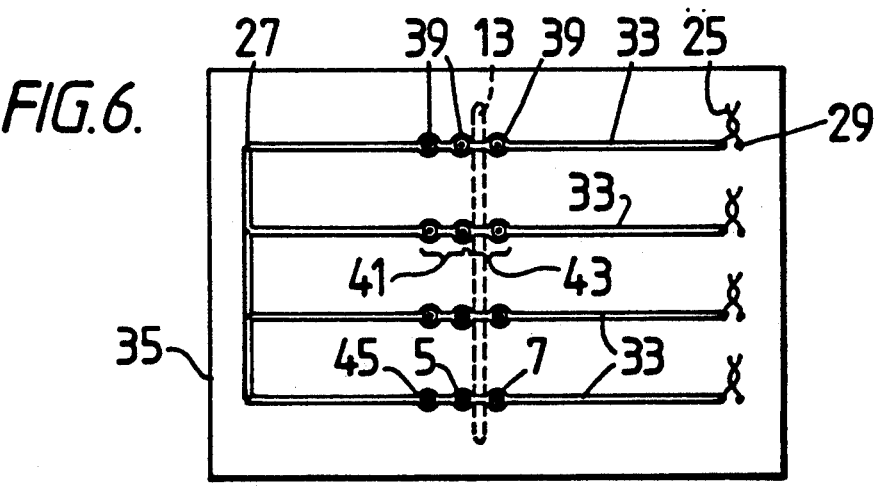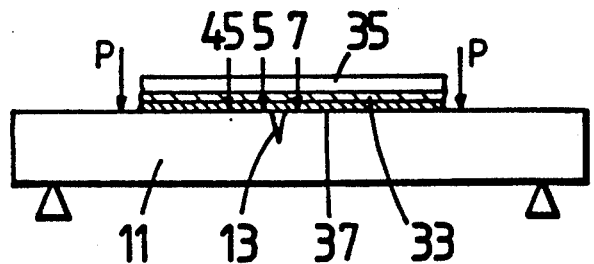

METHOD, TEST PROBE AND APPARATUS FOR THE MEASUREMENT OF ALTERNATING CURRENT POTENTIAL DROP BY CONFINING TEST CURRENT TO A SKIN REGION OF A TEST SPECIMEN

TECHNICAL FIELD

The present invention concerns improvements in and relating to methods, test probes and apparatus for the measurement of alternating current potential drop such as adopted for example in the monitoring and measurement of the depth of cracks generated in materials under strain.

Among the various techniques available for monitoring crack growth, the potential drop (PD) method has been widely used because it is relatively simple yet accurate. The PD technique depends on the relationship of the electrical resistance of a cracked body to and depth of the crack. The voltage drop across the crack generated by passing a constant current through the specimen is used to monitor the crack depth. Either direct or alternating current may be used to generate the voltage across the specimen (DCPD or ACPD respectively). The DCPD technique is more commonly used because of its apparent simplicity. The DCPD measurement however has several disadvantages which are effectively overcome by using ACPD.

The accuracy of measurement using the DCPD technique is limited by several errors as described below.

1. The resistance of a 25 mm thick compact tension (CT) steel specimen is a few $\Omega$. Large currents of the order of 30 to 100 amperes are therefore necessary to get a measurable signal. If the PD is to give a direct measure of resistance, then for accurate reproducible measurement of crack depth the drift in the value of this large current has to be kept to a minimum. To achieve a resolution of 0.01 mm in crack depth measurement, with a specimen geometry generally used, the current has to be constant to within $\pm 0.01\%$.
2. Thermoelectric voltages which are generated across the connections between the specimen and the measuring leads due to temperature differentials can be of the order of $\mu V$. In the case of iron/copper for example for a difference of only 1° C. between the measuring leads the thermal EMF is about 11 $\mu V$. This can cause an error of the order of 1 mm in crack depth measurement.
3. The voltage drift at the input of even a high quality d.c. differential amplifier can be of the order of 1 $\mu V$ per degree centigrade. A 5° C. variation of temperature during a test can therefore cause an error of about 0.5 mm in crack depth measurement.
4. A quite significant and often overlooked error is due to the large temperature coefficient of resistance of steel which is about $5 \times 10^{-3}$ per degree centigrade. The error caused by a 5° C. change in temperature would be about 2.5%.
5. Large currents can cause heating at the narrowest and the most important point, the crack tip, causing undesirable conditions leading to further errors in measurement.

Some of these errors can be minimized by interrupting or reversing the large d.c. current at regular intervals and subtracting out the error voltages. This however adds considerably to the complexity of the already bulky power supplies.

When a conductor carries an alternating current at high frequencies, the current flows near the surface of the conductor due to the "skin effect". The strength of this effect is given by the depth of penetration 6 which is termed the "skin depth". The stronger the skin effect the smaller the skin depth The skin depth is given by the relation $$\delta = \sqrt{\rho/\pi\mu f}$$ Equation 1 where $\rho$ is the resistivity, $\mu$ is the magnetic permeability and f is the frequency.

Advantages of ACPD over DCPD are:
1. Increased accuracy. It is not affected by thermoelectric voltages. It has a much greater signal to current ratio. Also phase sensitive detection may be employed readily to enhance signal over noise ratio.
2. Clearer indication of crack initiation. This is due to the greater sensitivity of ACPD (i.e. high signal to crack growth ratio) and its sensitivity to the onset of elastic and plastic strain.
3. Increased linearity between ACPD and crack length.
4. Negligible heating of the specimen due to the low currents used.
5. Simpler connections, more compact and more conventional equipment.

It is however essential to observe certain precautions whilst using ACPD. It is a problem that the output from the PD sensing leads in addition to the specimen potential drop also contain voltages picked up from the electromagnetic field radiated by the supply current to the specimen. If the electromagnetic pick-up is an appreciable fraction of potential drop voltage, it can affect the initial calibration and can cause discrepancies. This error becomes serious for non-magnetic materials (e.g. stainless steel or aluminium) where higher frequencies have to be used with a consequent increase in electromagnetic radiation and pick-up.

The accuracy of measurement can also be limited by crack geometry. For a short deep crack, the current can flow around the crack rather than into and out of it. It is a problem thus that significant corrections must then be applied to measurements taken to ensure a correct interpretation and measurement of crack depth.

DISCLOSURE OF THE INVENTION

The present invention is intended to provide a remedy.

The present invention has as an object thereof the provision of step and/or means to provide a further localization in the flow of current through the specimen. In this manner it is possible therefore to obviate or at least significantly reduce the need for and magnitude of corrections to be applied to take account of crack geometry The present invention has as a further object the provision of a step or means to provide a further confinement in the spread of the electromagnetic field that is associated with current flow in the specimen and in the leads conducting current to and from the specimen.

In accordance with a first aspect of the present invention there is provided a method of alternating current potential drop measurement in which a voltage signal is taken between a pair of spaced points on the surface of a test specimen whilst an electric current is passed through the same at such an alternating frequency that flow of the current is spatially confined to a skin region thereof, characterized in that said flow of the current is also laterally confined by passing said same current externally over and in immediate proximity to said surface of the test specimen.

In accordance with a further aspect of the present invention there is provided a voltage probe for use in the method aforesaid, which voltage probe includes:
- a first pair of longitudinally spaced voltage probe contacts; and
- first and second current contacts;

characterized by:
- a longitudinally extending isolated conductor which is arranged adjacent to the voltage probe contacts and is connected to said first current contact to provide an external flow path for current applied to said test specimen.

When the voltage probe aforesaid is used for measurement of the alternating current potential drop, there is an interaction between the electromagnetic field corresponding to the external flow of current in the conductor and the flow of current internally in the skin of the specimen. The effect of this interaction is to provide a lateral confinement of the current flowing in the specimen. The resultant alternating current potential drop measured thus is less sensitive to differences in the lateral extent of any crack that is measured. Furthermore, electromagnetic radiation corresponding to the flow of current in the external conductor and in the specimen is predominantly confined to an area bounded by the conductor and the specimen surface.

Additional and supplemental measures may be taken to provide compensation for any coupling of the residual electromagnetic radiation and the voltage probe. Such measures include the use of a compensating induction loop and phase sensitive detection using a reference voltage that is in phase with the applied alternating current.

BRIEF INTRODUCTION OF THE DRAWINGS

In the accompanying drawings:

FIG. 3 is a schematic cross-section of a test specimen, a probe and connected current leads arranged in particular manner in accord with the present invention;

FIG. 4 is an illustrative plan view of the arrangement shown in the preceding FIG;

FIG. 5 is a schematic enlarged field diagram to illustrate the current profile and field relationship for a conductor arranged in close proximity above the surface of a test specimen;

FIG. 6 is a plan view Of a printed circuit board, a part of a voltage probe configured in accord with the present invention;

FIG. 7 is a partial cross-section of the printed circuit board of the preceding FIG. as arranged in position over a test specimen;

DESCRIPTION OF PREFERRED EMBODIMENTS

Embodiments of the present invention will now be described and particular reference will be made to the accompanying drawings. The description that follows is given by way of example only.

Figure 1:
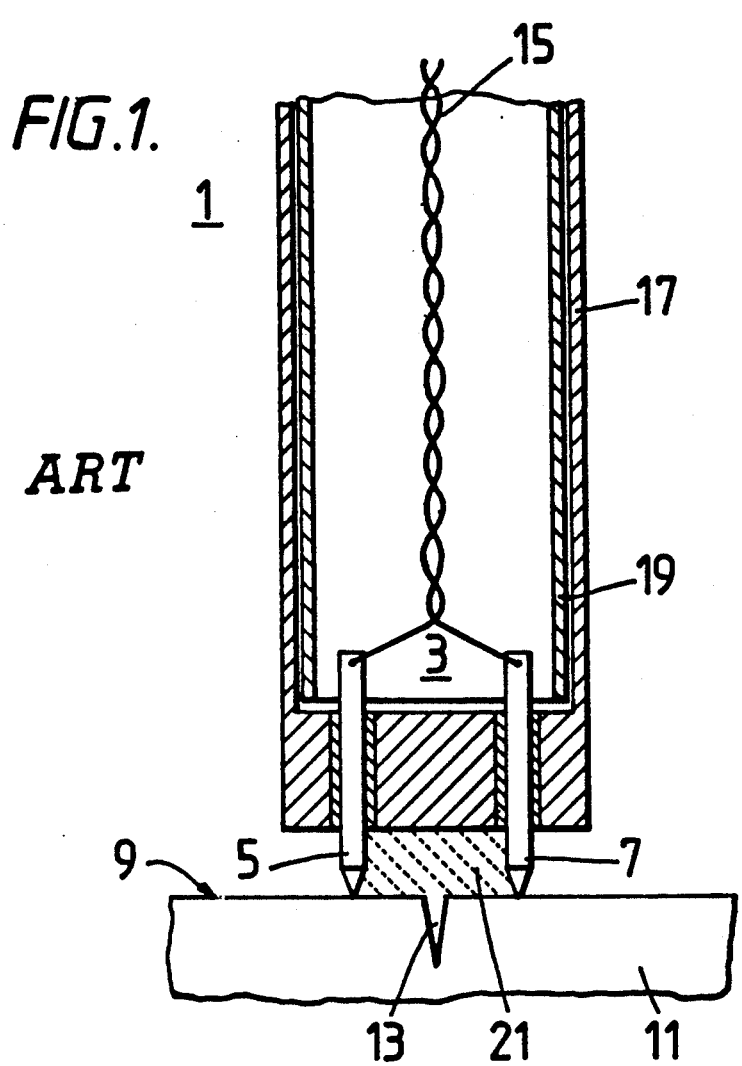
FIG. 1 is a schematic cross-section of a known voltage probe.

A handheld probe of typical construction is shown in FIG. 1. This probe 1 comprises a pair 3 of voltage probe contacts 5 and 7 arranged in contact with the surface 9 of a test specimen 11. The probe contacts 5 and 7 are arranged to each side of a crack 13 in the test specimen 11. The potential drop developed in the test specimen 11 between the voltage probe contacts 5 and 7 is picked up using a tightly twisted pair of conductors or a coaxial cable 15. The probe 1 further comprises a casing 17 of either thick copper or aluminium to shield the cable 15 from the influence of high frequency electromagnetic radiation. An inner shield 19, which may be of mu-metal, is also located within the casing 17 to afford shielding from low frequency electromagnetic radiation such as that generated in the vicinity of mains cable or adjacent equipment. In FIG. 1, shading has been used to denote an area 21 that is bounded above by the casing 17, below by the surface 9 of the specimen 11 and each side by the voltage probe contacts 5 and 7. Electromagnetic radiation corresponding to flow of current in a surface skin of the test specimen 11 is coupled to this area 21 and induces an error EMF that is also picked up in addition to the desired potential drop in the specimen 11.

Figure 2:
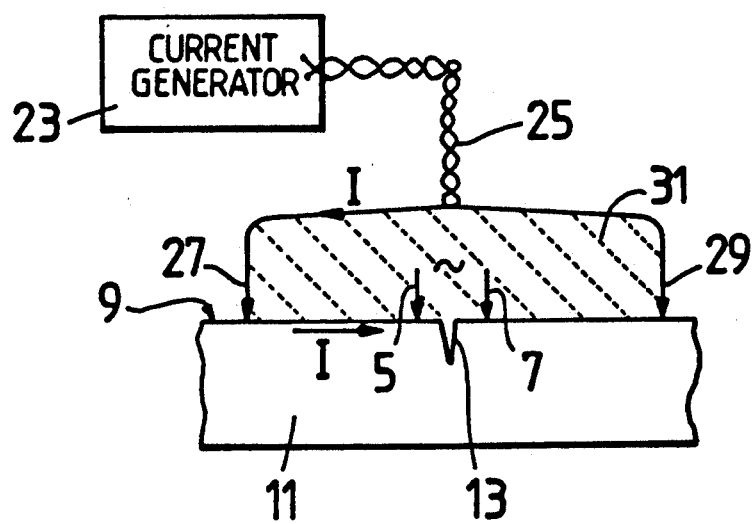
FIG. 2 is a schematic cross-sectional view showing a test specimen and connected current leads arranged in a conventional manner.

A typical current feed arrangement is shown in FIG. 2. Alternating current I, supplied from a current source 23, is applied to the surface 9 of the test specimen 11 by means of a tightly twisted pair or a coaxial cable 25 which latter is connected to current contact pins 27 and 29. A current loop 31 is defined by the current leads 27 and 29 and the specimen 11. This current loop is the source for most of the electromagnetic radiation. This arrangement is modified as shown in FIGS. 3 and 4. The return lead, a conductor 33, is placed as near as possible to the surface 9 of the specimen 11. This reduces the area 31 responsible for the EM radiation to a minimum and hence reduces the effect of the resulting radiation to a minimum likewise.

This arrangement has however another very important advantage. When current flows between two conductors, the energy is transmitted by an electromagnetic field between the two. The electromagnetic field penetrates the conducting surfaces of the conductors and causes the electrons to change position. The extent of the field's penetration depends upon frequency, magnetic permeability and electrical resistivity. As the current in the specimen 11 is concentrated in the region nearest to the return conductor 33 as shown in FIG. 5, the voltage probe contact pins 5 and 7 should be placed as near to the current lead 33 as possible to obtain maximum sensitivity. The sensitivity can be defined as a probe voltage $V_P$ divided by the current $I_Z$ flowing through the specimen 11.

Moreover if the length 1 of the crack 13 is short compared to its depth d, the probe voltage $V_P$ will be less than for an infinitely long crack but the correction factor required for this would be much less than that in a case where the return conductor is located further away from the surface of the specimen.

It is therefore important to bring the return lead 33 as near as possible to the surface 9 of the specimen 11. A practical mounting arrangement is shown in FIG. 6. Here a copper clad board 35 such as that used as the basis of a printed circuit board PCB covered with insulating lacquer or film 37 can be used to implement the return conductor 33.

Tracks 33 can be etched on the PCB 35 for conducting the current I and apertures 39 cut through the PCB 35 and the tracks 33 for receiving the voltage contact pins 5 and 7 which are to pass through the same and are to be isolated by spacing and filling from the conducting tracks 33. The mounting arrangement shown is useful for monitoring a number of voltages along the length of the crack 13 during testing (e.g. fatigue) of materials (see FIG. 7). FIG. 6, only four tracks 33 and two pairs 41,43 of voltage pick-up points 45,5 and 5,7 per track are shown. However, there could be ten, twenty or more such tracks on a plate specimen 11 under test. Under test conditions, a flexible PCB 35 partially glued to the test plate 11 can be used.

Figure 8:
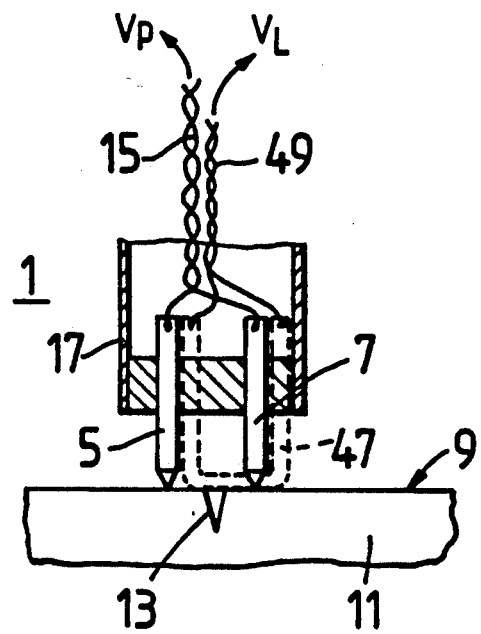
FIG. 8 is a schematic cross-section of a voltage probe including a compensation loop.
Figure 9:
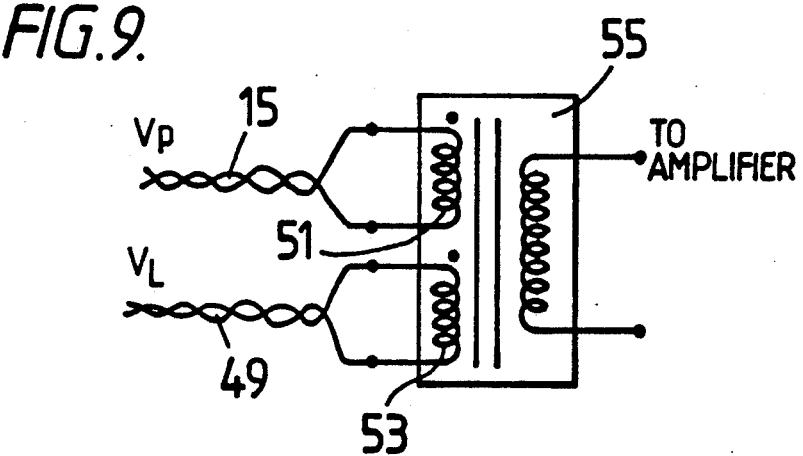
FIGS. 9 and 10 show schematic arrangements for combining measured and compensating voltages measured using the probe of the preceding FIG.

Additional measures may also be taken to further reduce the effects of electromagnetic coupling. As shown in FIG. 8, the probe 1 is modified by the provision of an additional loop 47 of wire which is arranged to enclose the same area 21 as that between the two probes 5 and 7. It is positioned as close to the probes 5 and 7 as possible so that the loop 47 picks up the same EMF as that induced in the area 21 between the probes 5 and 7. Preferably, connected leads 49 from the loop 47 should be arranged to run alongside or even be twisted with the principal leads 15 of the probe 1. The voltage $V_L$ picked up by this loop 47 is then subtracted from the voltage $V_P$ picked up in the probe circuit. The difference voltage $V_P - V_L$ is nearer to the true ACPD signal picked up by the probe 1.

Figure 10:
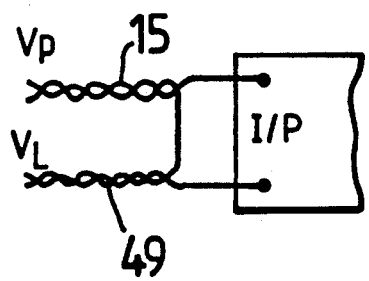

The subtraction can be carried out by connecting the output from the two pairs of the leads 15,49 in phase opposition (see FIG. 10) or better still by feeding it into two primaries 51,53 of an input transformer 55. Note that the small amount of induced voltage picked up by the shielded leads 15 and 49 will also be cancelled.

Alternatively, the subtraction or cancellation can also be carried out after feeding the voltages $V_P$ and $V_L$ into two separate preamplifiers. A difference amplifier could also be used as an alternative.

Figure 11:
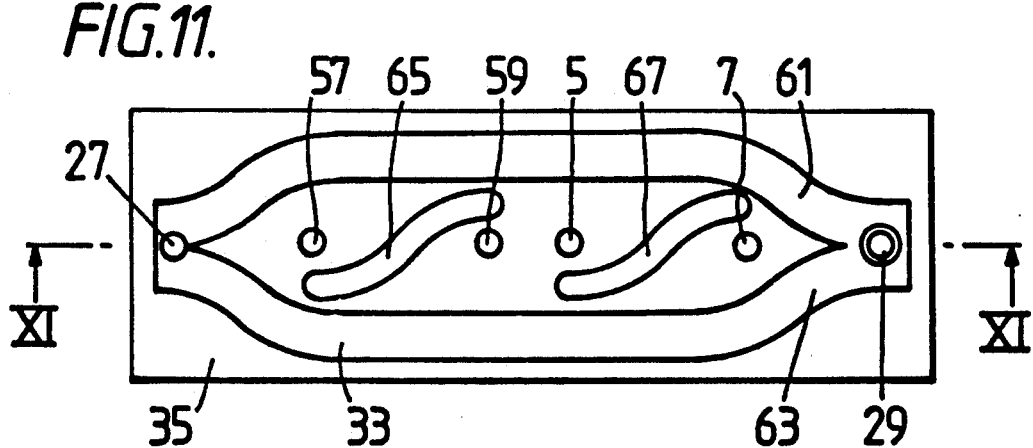
FIG. 11 is a plan view of a printed circuit board, part of a probe constructed in accord with this invention.
Figure 12:
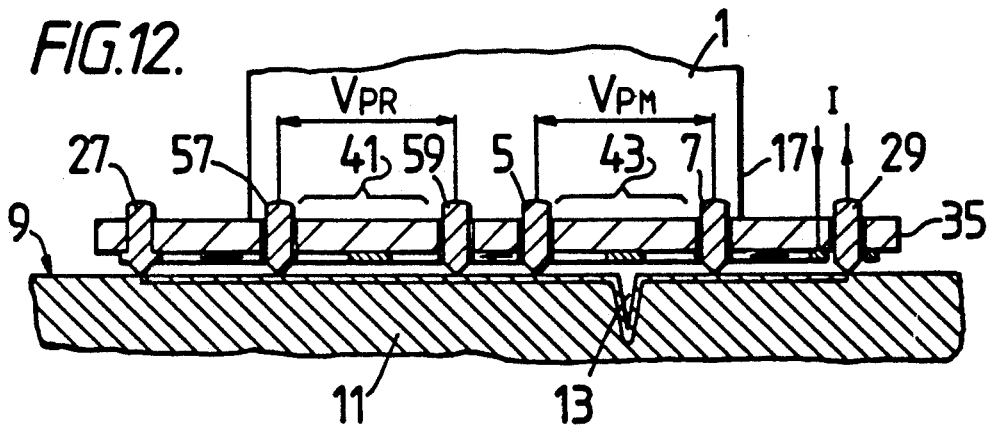
FIGS. 12 and 13 show in illustrative cross-section and in cut-out perspective the printed circuit board shown in the preceding FIG. 11.
Figure 13:
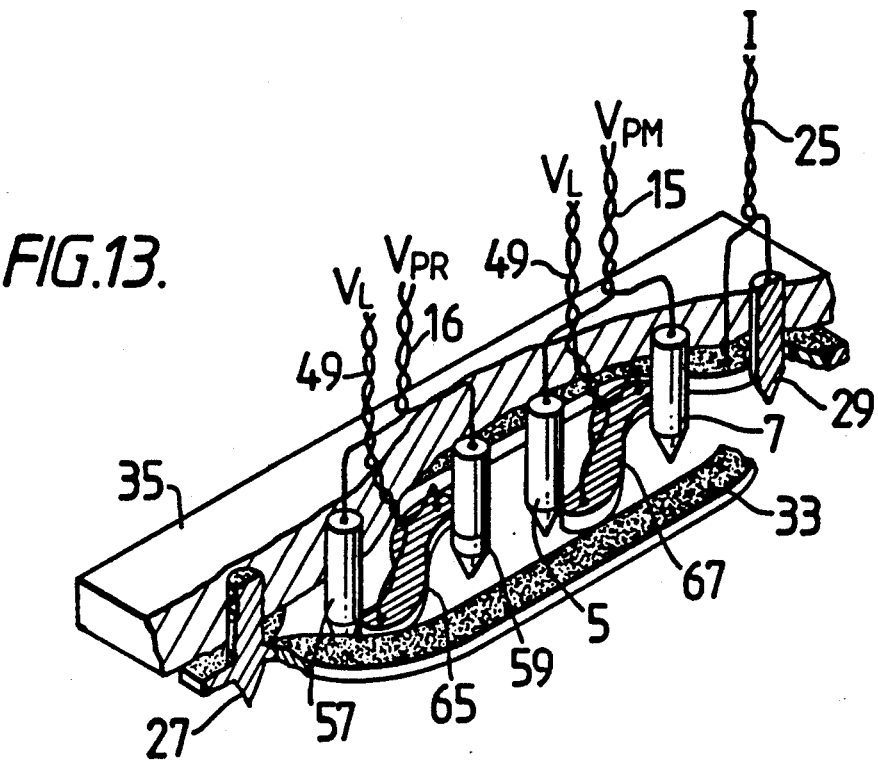
Figure 14:
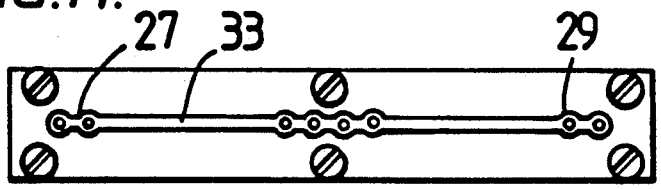
FIGS. 14 through 17 are bottom elevation, cross-section, top elevation and side elevation views of an engineered voltage probe made in accordance with the present invention.
Figure 15:
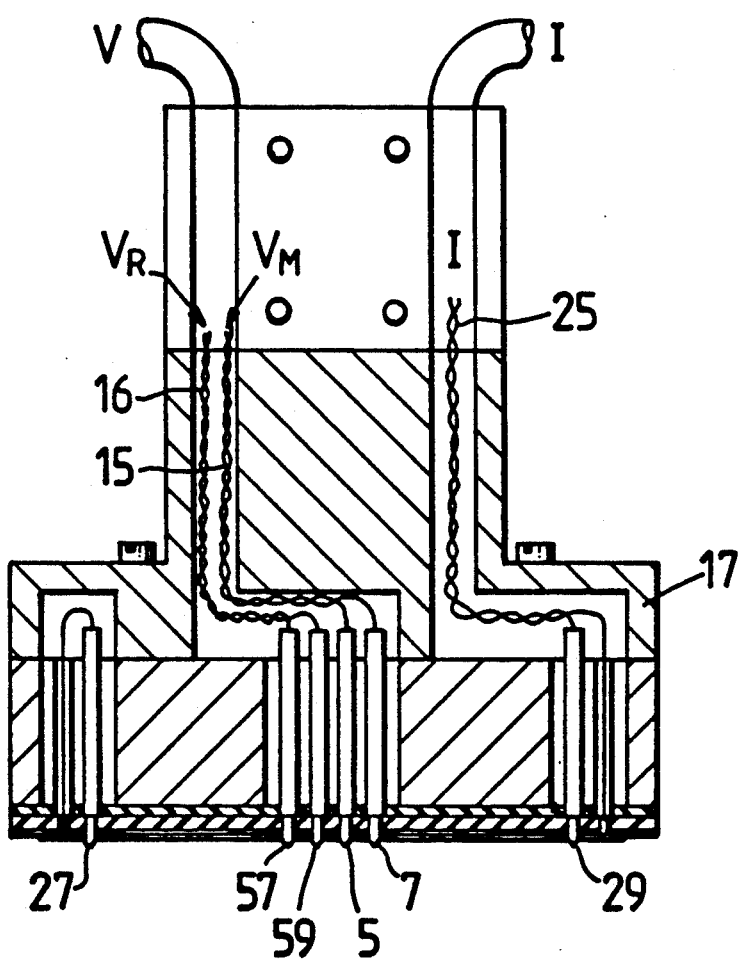
Figure 17:
Figure 16:
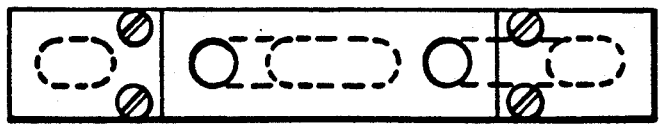

Both the features described above, the return conductor 33 and the loop 47 can be incorporated in a unitary probe design. A practical implementation is shown in FIGS. 11, 12 and 13.

In this unitary arrangement, two pairs 41 and 43 of probe contact pins 57 and 59, 5 and 7 are used, one pair 41 for measuring the ACPD voltage dro $V_{PR}$ over a flat portion of the surface 9 of the specimen 11 near to the crack 13 and the other pair 43 measuring the ACPD voltage dro $V_{PM}$ across the crack 13 itself. The contribution of the induced EMF is minimized by subtracting from $V_{PR}$ and $V_{PM}$ the voltage $V_L$ from respective loops 47 coincident with each pair 41,43 of the probe contact pins 57 and 59, 5 and 7. Provision is also made in the probe design for supplying the energizing current I. This current enters the probe 1 at the righthand end of the printed circuit board track 33 as seen in FIG. 12, travels through the track 33 which is bifurcated as shown and passes to a lefthand current contact pin 27 by which means it enters the specimen 11. It passes through the specimen 11 past the crack 13 and returns through a further current contact pin 29 at the righthand end of the probe 1. The voltages $V_{PR}$ and $V_{PM}$ are taken from the two pairs 41,43 of the probe voltage contact pins 57 and 59, 5 and 7 by means of twisted leads 16,15. The two pairs 41,43 of probe voltage contact pins 57 and 59, 5 and 7 are positioned between branches 61,63 of the printed circuit board track 33 as shown. Short length S-shaped tracks 65,67 which form part of each of the respective inductive loops 47 are arranged between the contact pins 57 and 59, 5 and 7 of each pair 41,43. Twisted leads 49 which are connected across each S-shaped track 65,67 are used to measure the compensating loop voltages $V_L$.

Bifurcation of the current conductor 33 has to be carried out because of the use of a single metallization of the PCB. If however a multi layer PCB is used, the compensating loop conductors 65,67 can be accommodated on a metallization layer that is superimposed over conductor 33.

A somewhat simpler engineered version of the voltage probe 1 is shown in FIGS. 14 through 17. In this simplified version, no provision has been made to include compensating inductive pick-up loops 47. It will be noted that all the probe contact pins 27,57,59,5,7 and 29 are spring-loaded so that the probe 1 can be pressed flat onto the surface 9 of the test specimen 11. The current carrying copper track 33 is covered with an insulating film and thus allows a minimum basing to be provided between the conductor 33 and the surface 9 of the specimen 11. When the probe is applied to the surface 9 of the test specimen 11, the conductor track 33 can thus be brought into immediate proximity with the surface 9 of the test specimen 11.

Figure 18:
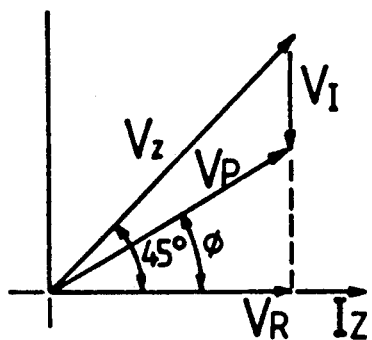
FIGS. 18 and 19 are vector diagrams showing resultant voltage measured for small and large induced voltage respectively.
Figure 19:
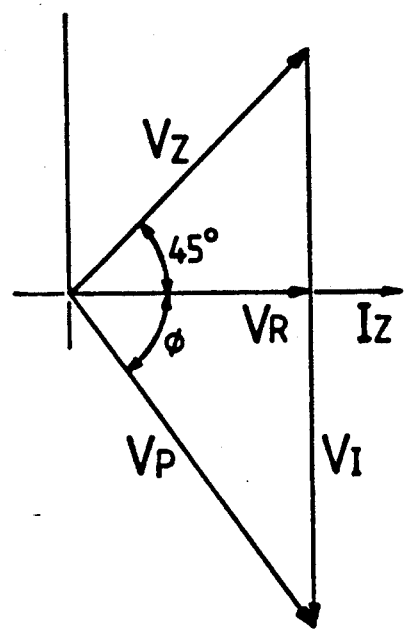

Yet one further measure can be taken to reduce the effect of electromagnetic radiation coupling. Thus it is possible to utilize the fact that when an alternating current is restricted to the surface of a metal by the "skin effect" the phase angle of the voltage between two points on this surface is at a constant angle 45° relative to the phase angle of the current; whereas the phase angle of the voltage due to inductive pick-up at the probes, as discussed earlier, is at 90° relative to the phase angle of the current. The relative phases are shown in FIGS. 18 and 19. In these FIGS. $I_Z$ is the current flowing through the specimen, $V_Z$ is the ACPD voltage, due to the skin effect, and $V_I$ is the inductive pick-up. The measured signal voltage between the probes, $V_P$, is a vector sum of $V_Z$ and $V_I$. Two cases are illustrated. In FIG. 18 $V_I$ is small compared to $V_Z$ and in FIG. 19 $V_I$ is large compared to $V_Z$.

Figure 20:
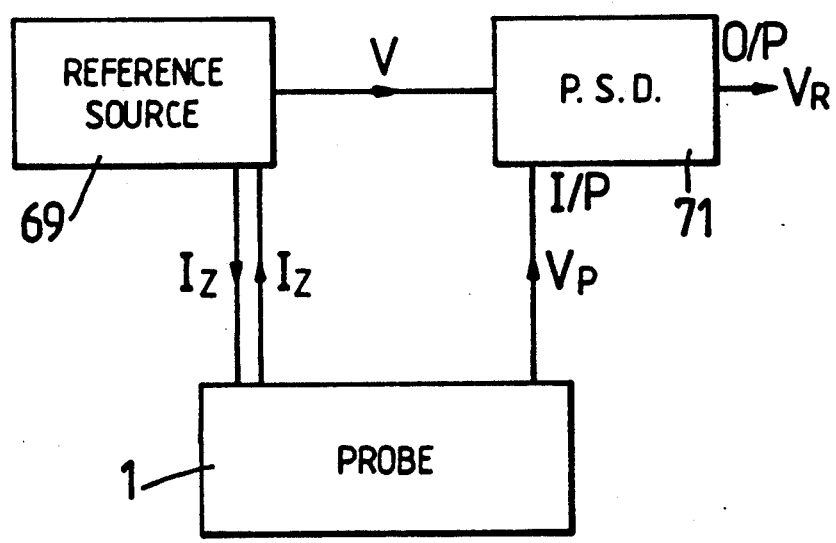
FIG. 20 is a simplified block diagram for apparatus comprising a probe, a current source and a phase sensitive detector.

The undesirable effect of the unavoidable inductive pick-up can be removed by using the real (i.e. resistive) component of the voltage signal for both measurement and calibration of the crack depth. Since phase sensitive detection is commonly used to detect and process probe voltage signals, a simple method of obtaining the resistive component $V_R$ would be to set the phase angle of a switching waveform applied to the phase sensitive detector in phase with the applied current $I_Z$. The output of the phase sensitive detector would now be proportional to $V_R$, the real part of the measured signal $V_P$. The arrangement of apparatus which comprises the probe 1, a reference source 69 for current and in-phase voltage and the phase sensitive detector 71 is shown in FIG. 20.

I claim:

1. A method of measuring alternating current potential drop in a specimen, comprising the steps of:
  a) passing an electric current between a pair of spaced contact means in contact with the specimen so as to supply said electric current through said specimen and so as to produce a voltage therein, said pair of contact means being spaced from each other in a first direction along said specimen, and said current having an alternating frequency which causes the flow of said electric current to be spatially confined to a skin region of said specimen; and
  b) passing said electric current through a conductor which extends substantially in said first direction and which is located so close to a surface of said specimen that current distribution in said skin region is influenced to cause the flow of said electric current through said specimen to be confined in a second direction substantially transverse to said first direction; and
  c) measuring the voltage between a pair of spaced points on the surface of the specimen.

2. The method of measuring as claimed in claim 1, further including the step of compensating for induced error emf present in the measured voltage by subtracting a corrective emf induced in a loop positioned close to said pair of spaced points.

3. The method of measuring as claimed in claim 1, further including the step of detecting the measured voltage using a phase sensitive detector to which a switching voltage waveform in phase with said electric current is applied.

4. A voltage probe comprising:
  first and second current contact means for applying a current to a specimen to produce a voltage in said specimen, said current contact means being separated along a first direction of said specimen when applying said current thereto;
  isolated conductor means extending in said first direction for providing an external flow path for current applied to the specimen, said conductor means being supplied with current from said first current contact means and returning said current to said second current contact means; and
  a first pair of voltage probe contact means for measuring the voltage induced by said current contact means in said specimen, said voltage probe contact means being arranged adjacent to said conductor means and being spaced from each other along said first direction.

5. The voltage probe as claimed in claim 4, including a flexible support on which said conductor means is mounted.

6. The voltage probe as claimed in claim 5, wherein the flexible support is a printed circuit board, said conductor means being provided by a first conductive track defined thereon.

7. The voltage probe as claimed in claim 6, wherein the printed circuit board is apertured to receive each of aid first pair of voltage probe contact means.

8. The voltage probe as claimed in claim 7, wherein said first conductive track is bifurcated 61,63 and passes each side of aid first pair 43 of voltage probe contact means.

9. The voltage probe as claimed in claim 1 including a first compensation emf loop.

10. The voltage probe as claimed in claim 6 including a first compensation emf loop wherein a second conductive track on said printed circuit board is incorporated as a part of said first loop 47.

11. The voltage probe as claimed in claim 10, wherein said first conductive track is bifurcated passes each side of said first pair 43 of voltage probe contact means, and passes each side of said second conductive track.

12. The voltage probe as claimed in claim 4 including a second pair of longitudinally spaced voltage probe contact means.

13. The voltage probe, as claimed in claim 10, including a second pair of longitudinally spaced voltage probe contact means, a second compensation emf loop wherein a third conductive track on said printed circuit board is incorporated as a part of said second loop, said first conductive track 33 is bifurcated, passes each side of said first and second pairs of voltage probe contact means, and passes each side of said second and third conductive tracks.

14. Apparatus for the measurement of alternating current potential drop, said apparatus comprising:
  a voltage probe including:
  first and second current contact means for applying a current to a specimen to produce a voltage in said specimen, said current contact means being separated along a first direction of said specimen when applying said current thereto;
  isolated conductor means extending in said first direction for providing an external flow path for current applied to the specimen, said conductor means being supplied with current from said first current contact means and returning said current to said second current contact means; and
  a first pair of voltage probe contact means for measuring the voltage induced by said current contact means in said specimen, said voltage probe contact means being arranged adjacent to said conductor means and being spaced from each other along said first direction;
  current source means for passing alternating current through said conductor means and said second current contact means, said current source means being connected to said conductor means and said second current contact means; and
  phase sensitive detector means arranged relative to said current source means for receiving a voltage in phase with said alternating current, and arranged relative to said first pair of voltage probe contact means for receiving a voltage signal therefrom.

* * * * *

UNITED STATES PATENT AND TRADEMARK OFFICE
CERTIFICATE OF CORRECTION

PATENT NO. : 5,202,641
DATED : APRIL 13, 1993
INVENTOR(S) : BHIKHU A. UNVALA

It is certified that error appears in the above-identified patent and that said Letters Patent is hereby corrected as shown below:

Column 8, line 10, change "aid" to --said--;

line 12, cancel "61,63";

line 13, cancel "43";

line 15, change "1" to --4--;

line 20, cancel "47";

line 23, cancel "43";

line 22, after "bifurcated" insert --,--;

line 28, cancel ",";

Signed and Sealed this

Eleventh Day of January, 1994

Attest:

BRUCE LEHMAN

Attesting Officer      Commissioner of Patents and Trademarks